US005723309A

United States Patent [19]

Bonneville

[11] Patent Number: 5,723,309

[45] Date of Patent: Mar. 3, 1998

[54] PRODUCTION OF SUBUNITS OF SOLUBLE T CELL RECEPTORS BY CO-TRANSFECTION

[75] Inventor: Marc Bonneville, Nantes Cedex, France

[73] Assignees: Institut National de la Sante et de la Recherche Medicale (INSERM), Paris Cedex; Immunotech, Marseille Cedex, both of France

[21] Appl. No.: 256,964

[22] PCT Filed: Nov. 25, 1993

[86] PCT No.: PCT/FR93/01165

§ 371 Date: Sep. 14, 1994

§ 102(e) Date: Sep. 14, 1994

[87] PCT Pub. No.: WO94/12648

PCT Pub. Date: Jun. 9, 1994

[30] Foreign Application Priority Data

Nov. 25, 1992 [FR] France .................................... 92 14203

[51] Int. Cl.[6] ........................... C12N 15/12; C12N 15/63; C12N 15/79; C12N 15/87

[52] U.S. Cl. .............................. 435/69.1; 435/4; 435/7.1; 435/69.52; 435/69.7; 435/172.3

[58] Field of Search ................................ 435/4, 7.1, 69.1, 435/69.52, 69.7, 172.3; 424/85.2; 514/8

[56] References Cited

U.S. PATENT DOCUMENTS 5,314,995 5/1994 Fell, Jr. et al. ......................... 530/351

FOREIGN PATENT DOCUMENTS

| | | |
|---|---|---|
| WO 88/00209 | 1/1988 | WIPO . |
| WO 89/03996 | 5/1989 | WIPO . |
| WO 91/10438 | 7/1991 | WIPO . |
| WO 91/18019 | 11/1991 | WIPO . |

OTHER PUBLICATIONS

"Heterodimeric, disulfide–linked alpha/bata T cell receptors in solution", *European Journal of Immunology*, vol. 21, No. 1, 1991, VCH Verlagsgesellschaft, Germany, by Alfred E. Slanetz et al., pp. 179–183.

"Engineered secreted T–cell receptor alpha beta heterodimers", *Proceedings of the National Academy of Sciences of USA*, vol. 88, No. 18, 1991, Washington by Claude Gregorie et al., pp. 8077–8081.

"A soluble, single–chain T–cell receptor arrangement endowed with antigen–combining properties", *Proceedings of the National Academy of Sciences of USA*, vol. 88, No. 19, 1991, Washington, by Jiri Novotny et al., pp. 8646–8650.

Sambrook et al. 1989, *Molecular Cloning*, pp. 15.51–15.52 Cold Spring Harbor Laboratory Press, NY.

Goverman et al. 1991, Basic & Clinical Immunol., ed. by Strites & Terr. Norwalk, CT, Appleton and Lange, pp. 73–77.

Chien et al. 1993, Immunology Today 14:597–602.

*Primary Examiner*—Vasu S. Jagannathan
*Assistant Examiner*—Elizabeth C. Kemmerer
*Attorney, Agent, or Firm*—Young & Thompson

[57] ABSTRACT

Soluble, single chain T cell receptors, nucleic acid sequences, particularly DNA sequences, encoding the soluble, single chain T cell receptor, expression vectors containing the DNA sequences, and host cells containing the expression vectors.

10 Claims, 6 Drawing Sheets

16 / 1 46 / 11
ATG CAG AGG ATC TCC TCC CTC ATC CAT CTC TCT CTC TTC TGG GCA GGA GTC ATG TCA GCC
met gln arg ile ser ser leu ile his leu ser leu phe trp ala glv val met ser ala
76 / 21 106 / 31
ATT GAC TTG GTG CCT GAA CAC CAA ACA GTG CCT GTG TCA ATA GGG GTC CCT GCC ACC CTC
ile glu leu val pro glu his gln thr val pro val ser ile gly val pro ala thr leu
136 / 41 166 / 51
AGG TGC TCC ATG AAA GGA GAA GCG ATC GGT AAC TAC TAT ATC AAC TGG TAC AGG AAG ACC
arg cys ser met lys gly glu ala ile gly asn tyr tyr ile asn trp tyr arg lys tnr
196 / 61 226 / 71
CAA GCT AAC ACA ATG ACT TTC ATA TAC CGA GAA AAG GAC ATC TAT GGC CCT CCT TTC AAA
gln gly asn thr met thr phe ile tyr arg glu lys asp ile tyr gly pro gly pne lys
256 / 81 286 / 91
GAC AAT TTC CAA GGT GAC ATT GAT ATT GCA AAG AAC CTG GCT GTA CTT AAG ATA CTT GCA
asp asn phe gln gly asp ile asp ile ala lys asn leu ala val leu lvs ile leu ala
316 / 101 346 / 111
CCA TCA GAG AGA GAT GAA GGG TCT TAC TAC TGT GCC TGT GAC ACC TTG GGG ATG GGG GGG
pro ser glu arg asp glu gly ser tyr tyr cys ala cys asp thr leu gly met gly gly
376 / 121 406 / 131
GAA TAC ACC GAT AAA CTC ATC TTT GGA AAA GGA ACC CGT GTG ACT GTG GAA CCA AGA AGT
glu tyr thr asp lys leu ile pne gly lys gly thr arq val thr val glu pro arg ser
436 / 141 466 / 151
CAG CCT CAT ACC AAA CCA TCC GTT TTT GTC ATG AAA AAT GGA ACA AAT GTC GCT TGT CTG
gin pro nis tnr lys pro ser val pne val met lys asn gly thr asn vla ala cys leu
496 / 161 526 / 171
GTG AAG GAA TTC TAC CCC AAG GAT ATA AGA ATA AAT CTC GTG TCA TCC AAS AAG ATA ACA
val lys glu phe tyr pro lys asp ile arg ile asn leu val ser ser lys lys ile tnr
556 / 181 586 / 191
GAG TTT GAT CCT GCT ATT GTC ATC TCT CCC AGT GGG AAG TAC AAT GCT GTC AAG CTT GGT
glu pne asp pro ala ile val ile ser pro ser gly lys tyr asn ala val lys leu gly
616 / 201 646 / 211
AAA TAT GAA GAT TCA AAT TCA GTG ACA TGT TCA GTT CAA CAC GAC AAT AAA ACT GTG CAC
lys tyr glu asp ser asn ser val thr cys ser val gln his asp asn lys thr val his
676 / 221 706 / 231
TCC ACT GAC TTT GAA GTG AAG ACA GAT TCT ACA GAT CAC GTA AAA CCA AAG GAA ACT GAA
ser thr asp phe glu val lys thr asp ser thr asp his val lys pro lys glu thr glu
736 / 241 766 / 251
AAC ACA AAG CAA CCT TCA AAG AGC TGC CAT AAA CCC AAA GCC ATA GTT CAT ACC GAG AAG
asn thr lys gln pro ser lys ser cys his lys pro lys ala ile val his thr glu lys
796 / 261
TAA
OCH

FIG. 2A

```
12   /   1                              42   /   11
ATG CTG TCA CTG CTC CAC GCA TCA ACG CTG GCA GTC CTT GGG GCT CTG TGT GTA TAT GGT
met leu ser leu leu his ala ser thr leu ala val leu gly ala leu cys val tyr gly
72   /   21                             102  /   31
GCA GGT CAC CTA GAG CAA CCT CAA ATT TCC AGT ACT AAA ACG CTG TCA AAA ACA GCC CGC
ala gly his leu glu gln pro gln ile ser ser thr lys thr leu ser lys thr ala arg
132  /   41                             162  /   51
CTG GAA TGT GTG GTG TCT GGA ATA ACA ATT TCT GCA ACA TCT GTA TAT TGG TAT CGA GAG
leu glu cys val val ser gly ile thr ile ser ala thr ser val tyr trp tyr arg glu
192  /   61                             222  /   71
AGA CCT GGT GAA GTC ATA CAG TTC CTG GTG TCC ATT TCA TAT GAC GGG ACT GTC AGA AAG
arg pro gly glu val ile gln phe leu val ser ile ser tyr asp gly thr val arg lys
252  /   81                             282  /   91
GAA TCC GGC ATT CCG TCA GGC AAA TTT GAG GTG GAT AGG ATA CCT GAA ACG TCT ACA TCC
glu ser gly ile pro ser gly lys phe glu val asp arg ile pro glu thr ser thr ser
312  /   101                            342  /   111
ACT CTC ACC ATT CAC AAT GTA GAG AAA CAG GAC ATA GCT ACC TAC TAC TGT GCC TTG TGG
thr leu thr ile his asn val glu lys gln asp ile ala thr tyr tyr cys ala leu trp
372  /   121                            402  /   131
GAG GCC CAG CAA GAG TTG GGC AAA AAA ATC AAG GTA TTT GGT CCC GGA ACA AAG CTT ATC
glu ala gln gln glu leu gly lys lys ile lys val phe gly pro gly thr lys leu ile
432  /   141                            462  /   151
ATT ACA GAT AAA CAA CTT GAT GCA GAT GTT TCC CCC AAG CCC ACT ATT TTT CTT CTT TCA
ile thr asp lys gln leu asp ala asp val ser pro lys pro thr ile phe leu pro ser
492  /   161                            522  /   171
ATT GCT GAA ACA AAG CTC CAG AAG GCT GGA ACA TAC CTT TGT CTT CTT GAG AAA TTT TTC
ile ala glu thr lys leu gln lys ala gly thr tyr leu cys leu leu glu lys phe phe
552  /   181                            582  /   191
CCT GAT GTT ATT AAG ATA CAT TGG GAA GAA AAG AAG AGC AAC ACG ATT CTG GGA TCC CAG
prc asp val ile lys ile his trp glu glu lys lys ser ash thr ile leu gly ser gln
612  /   201                            642  /   211
GAG GGG AAC ACC ATG AAG ACT AAT GAC ACA TAC ATG AAA TTT AGC TGG TTA ACG GTG CCA
glu gly asn thr met lys thr asn asp thr tyr met lys phe set trp leu thr val pro
672  /   221                            702  /   231
GAA AAG TCA CTG GAC AAA GAA CAC AGA TGT ATC GTC AGA CAT GAG AAT AAT AAA AAC GCA
glu lys ser leu asp lys glu his arg cys ile val arg his glu asn asn lys asn gly
732  /   241                            762  /   251
GTT GAT CAA GAA ATT ATC TTT CCT CCA ATA AAG ACA GAT GTC ATC ACA ATG GAT CCC AAA
val asp gln glu ile ile phe pro pro ile lys thr asp val ile thr met asp pro lys
792  /   261                            822  /   271
GAC AAT TGT TCA AAA GAT GCA AAT GAT ACA CTA CTG CTG CAG TAA
asp asn cys ser lys asp ala asn asp thr leu leu leu gln OCH
```

FIG. 2B

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:1:

GGGTTACTGC AGCAGTAGTG TATC 24

( 2 ) INFORMATION FOR SEQ ID NO:2:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:2:

CCCTCGAGAT GCTGTTGGCT CTAGCTC 27

( 2 ) INFORMATION FOR SEQ ID NO:3:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:3:

TGTGCCACCT GGGACAGTCA TTATTATAAG AAACTCTTT 39

( 2 ) INFORMATION FOR SEQ ID NO:4:

-continued ( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:4:

GGGTTACTTC TCGGTATGAA CTATGGC 27

( 2 ) INFORMATION FOR SEQ ID NO:5:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:5:

GACTCGAGAA AAGATGATTC TTACTGTGGG 30

( 2 ) INFORMATION FOR SEQ ID NO:6:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:6:

ACTTACTGTC CTTTTTCCCG GCTCTTGGGG GACACCGATA AA 42

( 2 ) INFORMATION FOR SEQ ID NO:7:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: DNA (genomic)

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:7:

TGTGCTCTTG GGGACTTCCT AAAGGGTTCA GGTACCACCT ATCCATGGGA ACTCATCTTT 60

( 2 ) INFORMATION FOR SEQ ID NO:8:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:8:

CTCCCGGGGA GTGAGCCATG CAGAGG 26

( 2 ) INFORMATION FOR SEQ ID NO:9:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..48

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:9:

```
AGC TGC CAT AAA CCC AAA GCC ATA GTT CAT ACC GAG AAG GTG AAC ATG      48
Ser Cys His Lys Pro Lys Ala Ile Val His Thr Glu Lys Val Asn Met
  1               5                  10                  15
```

( 2 ) INFORMATION FOR SEQ ID NO:10:

( i ) SEQUENCE CHARACTERISTICS:
( A ) LENGTH: 16 amino acids
( B ) TYPE: amino acid
( D ) TOPOLOGY: linear ( i i ) MOLECULE TYPE: protein ( x i ) SEQUENCE DESCRIPTION: SEQ ID NO:10:

```
Ser Cys His Lys Pro Lys Ala Ile Val His Thr Glu Lys Val Asn Met
  1               5                  10                  15
```

( 2 ) INFORMATION FOR SEQ ID NO:11:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:11:

CGGTATCAAG TATGGCTCTT CATTGGG 27

( 2 ) INFORMATION FOR SEQ ID NO:12:

-continued ( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:12:

AGCCCGGGCA GACATGCTGT CACTGC 26

( 2 ) INFORMATION FOR SEQ ID NO:13:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..48

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:13:

```
AAT TGT TCA AAA GAT GCA AAT GAT ACA CTA CTG CTG CAG CTC ACA AAC     48
Asn Cys Ser Lys Asp Ala Asn Asp Thr Leu Leu Leu Gln Leu Thr Asn
  1               5                  10                  15
```

( 2 ) INFORMATION FOR SEQ ID NO:14:

( i ) SEQUENCE CHARACTERISTICS:
( A ) LENGTH: 16 amino acids
( B ) TYPE: amino acid
( D ) TOPOLOGY: linear ( i i ) MOLECULE TYPE: protein ( x i ) SEQUENCE DESCRIPTION: SEQ ID NO:14:

```
Asn Cys Ser Lys Asp Ala Asn Asp Thr Leu Leu Leu Gln Leu Thr Asn
  1               5                  10                  15
```

( 2 ) INFORMATION FOR SEQ ID NO:15:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:15:

CTATGTGATG ACGACGTCAT TGGG 24

-continued ( 2 ) INFORMATION FOR SEQ ID NO:16:

( i ) SEQUENCE CHARACTERISTICS:
( A ) LENGTH: 783 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..783

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:16:

```
ATG CAG AGG ATC TCC TCC CTC ATC CAT CTC TCT CTC TTC TGG GCA GGA      48
Met Gln Arg Ile Ser Ser Leu Ile His Leu Ser Leu Phe Trp Ala Gly
  1               5                  10                  15

GTC ATG TCA GCC ATT GAG TTG GTG CCT GAA CAC CAA ACA GTG CCT GTG      96
Val Met Ser Ala Ile Glu Leu Val Pro Glu His Gln Thr Val Pro Val
             20                  25                  30

TCA ATA GGG GTC CCT GCC ACC CTC AGG TGC TCC ATG AAA GGA GAA GCG     144
Ser Ile Gly Val Pro Ala Thr Leu Arg Cys Ser Met Lys Gly Glu Ala
         35                  40                  45

ATC GGT AAC TAC TAT ATC AAC TGG TAC AGG AAG ACC CAA GGT AAC ACA     192
Ile Gly Asn Tyr Tyr Ile Asn Trp Tyr Arg Lys Thr Gln Gly Asn Thr
     50                  55                  60

ATG ACT TTC ATA TAC CGA GAA AAG GAC ATC TAT GGC CCT GGT TTC AAA     240
Met Thr Phe Ile Tyr Arg Glu Lys Asp Ile Tyr Gly Pro Gly Phe Lys
 65                  70                  75                  80

GAC AAT TTC CAA GGT GAC ATT GAT ATT GCA AAG AAC CTG GCT GTA CTT     288
Asp Asn Phe Gln Gly Asp Ile Asp Ile Ala Lys Asn Leu Ala Val Leu
                 85                  90                  95

AAG ATA CTT GCA CCA TCA GAG AGA GAT GAA GGG TCT TAC TAC TGT GCC     336
Lys Ile Leu Ala Pro Ser Glu Arg Asp Glu Gly Ser Tyr Tyr Cys Ala
            100                 105                 110

TGT GAC ACC TTG GGG ATG GGG GGG GAA TAC ACC GAT AAA CTC ATC TTT     384
Cys Asp Thr Leu Gly Met Gly Gly Glu Tyr Thr Asp Lys Leu Ile Phe
        115                 120                 125

GGA AAA GGA ACC CGT GTG ACT GTG GAA CCA AGA AGT CAG CCT CAT ACC     432
Gly Lys Gly Thr Arg Val Thr Val Glu Pro Arg Ser Gln Pro His Thr
    130                 135                 140

AAA CCA TCC GTT TTT GTC ATG AAA AAT GGA ACA AAT GTC GCT TGT CTG     480
Lys Pro Ser Val Phe Val Met Lys Asn Gly Thr Asn Val Ala Cys Leu
145                 150                 155                 160

GTG AAG GAA TTC TAC CCC AAG GAT ATA AGA ATA AAT CTC GTG TCA TCC     528
Val Lys Glu Phe Tyr Pro Lys Asp Ile Arg Ile Asn Leu Val Ser Ser
                165                 170                 175

AAG AAG ATA ACA GAG TTT GAT CCT GCT ATT GTC ATC TCT CCC AGT GGG     576
Lys Lys Ile Thr Glu Phe Asp Pro Ala Ile Val Ile Ser Pro Ser Gly
            180                 185                 190

AAG TAC AAT GCT GTC AAG CTT GGT AAA TAT GAA GAT TCA AAT TCA GTG     624
Lys Tyr Asn Ala Val Lys Leu Gly Lys Tyr Glu Asp Ser Asn Ser Val
        195                 200                 205

ACA TGT TCA GTT CAA CAC GAC AAT AAA ACT GTG CAC TCC ACT GAC TTT     672
Thr Cys Ser Val Gln His Asp Asn Lys Thr Val His Ser Thr Asp Phe
    210                 215                 220

GAA GTG AAG ACA GAT TCT ACA GAT CAC GTA AAA CCA AAG GAA ACT GAA     720
Glu Val Lys Thr Asp Ser Thr Asp His Val Lys Pro Lys Glu Thr Glu
225                 230                 235                 240
```

-continued

| | | | | | | | | | | | | | | | | |
|---|---|---|---|---|---|---|---|---|---|---|---|---|---|---|---|---|
| AAC | ACA | AAG | CAA | CCT | TCA | AAG | AGC | TGC | CAT | AAA | CCC | AAA | GCC | ATA | GTT | 768 |
| Asn | Thr | Lys | Gln | Pro | Ser | Lys | Ser | Cys | His | Lys | Pro | Lys | Ala | Ile | Val | |
| | | | | 245 | | | | | 250 | | | | | 255 | | |
| CAT | ACC | GAG | AAG | TAA | | | | | | | | | | | | 783 |
| His | Thr | Glu | Lys | | | | | | | | | | | | | |
| | | | 260 | | | | | | | | | | | | | |

( 2 ) INFORMATION FOR SEQ ID NO:17:

( i ) SEQUENCE CHARACTERISTICS:
( A ) LENGTH: 260 amino acids
( B ) TYPE: amino acid
( D ) TOPOLOGY: linear ( i i ) MOLECULE TYPE: protein ( x i ) SEQUENCE DESCRIPTION: SEQ ID NO:17:

| | | | | | | | | | | | | | | | |
|---|---|---|---|---|---|---|---|---|---|---|---|---|---|---|---|
| Met | Gln | Arg | Ile | Ser | Ser | Leu | Ile | His | Leu | Ser | Leu | Phe | Trp | Ala | Gly |
| 1 | | | | 5 | | | | | 10 | | | | | 15 | |
| Val | Met | Ser | Ala | Ile | Glu | Leu | Val | Pro | Glu | His | Gln | Thr | Val | Pro | Val |
| | | | 20 | | | | | 25 | | | | | 30 | | |
| Ser | Ile | Gly | Val | Pro | Ala | Thr | Leu | Arg | Cys | Ser | Met | Lys | Gly | Glu | Ala |
| | | 35 | | | | | 40 | | | | | 45 | | | |
| Ile | Gly | Asn | Tyr | Tyr | Ile | Asn | Trp | Tyr | Arg | Lys | Thr | Gln | Gly | Asn | Thr |
| | 50 | | | | | 55 | | | | | 60 | | | | |
| Met | Thr | Phe | Ile | Tyr | Arg | Glu | Lys | Asp | Ile | Tyr | Gly | Pro | Gly | Phe | Lys |
| 65 | | | | | 70 | | | | | 75 | | | | | 80 |
| Asp | Asn | Phe | Gln | Gly | Asp | Ile | Asp | Ile | Ala | Lys | Asn | Leu | Ala | Val | Leu |
| | | | | 85 | | | | | 90 | | | | | 95 | |
| Lys | Ile | Leu | Ala | Pro | Ser | Glu | Arg | Asp | Glu | Gly | Ser | Tyr | Tyr | Cys | Ala |
| | | | 100 | | | | | 105 | | | | | 110 | | |
| Cys | Asp | Thr | Leu | Gly | Met | Gly | Gly | Glu | Tyr | Thr | Asp | Lys | Leu | Ile | Phe |
| | | 115 | | | | | 120 | | | | | 125 | | | |
| Gly | Lys | Gly | Thr | Arg | Val | Thr | Val | Glu | Pro | Arg | Ser | Gln | Pro | His | Thr |
| | 130 | | | | | 135 | | | | | 140 | | | | |
| Lys | Pro | Ser | Val | Phe | Val | Met | Lys | Asn | Gly | Thr | Asn | Val | Ala | Cys | Leu |
| 145 | | | | | 150 | | | | | 155 | | | | | 160 |
| Val | Lys | Glu | Phe | Tyr | Pro | Lys | Asp | Ile | Arg | Ile | Asn | Leu | Val | Ser | Ser |
| | | | | 165 | | | | | 170 | | | | | 175 | |
| Lys | Lys | Ile | Thr | Glu | Phe | Asp | Pro | Ala | Ile | Val | Ile | Ser | Pro | Ser | Gly |
| | | | 180 | | | | | 185 | | | | | 190 | | |
| Lys | Tyr | Asn | Ala | Val | Lys | Leu | Gly | Lys | Tyr | Glu | Asp | Ser | Asn | Ser | Val |
| | | 195 | | | | | 200 | | | | | 205 | | | |
| Thr | Cys | Ser | Val | Gln | His | Asp | Asn | Lys | Thr | Val | His | Ser | Thr | Asp | Phe |
| | 210 | | | | | 215 | | | | | 220 | | | | |
| Glu | Val | Lys | Thr | Asp | Ser | Thr | Asp | His | Val | Lys | Pro | Lys | Glu | Thr | Glu |
| 225 | | | | | 230 | | | | | 235 | | | | | 240 |
| Asn | Thr | Lys | Gln | Pro | Ser | Lys | Ser | Cys | His | Lys | Pro | Lys | Ala | Ile | Val |
| | | | | 245 | | | | | 250 | | | | | 255 | |
| His | Thr | Glu | Lys | | | | | | | | | | | | |
| | | | 260 | | | | | | | | | | | | |

( 2 ) INFORMATION FOR SEQ ID NO:18:

( i ) SEQUENCE CHARACTERISTICS:
( A ) LENGTH: 825 base pairs
( B ) TYPE: nucleic acid
( C ) STRANDEDNESS: single
( D ) TOPOLOGY: linear -continued ( i i ) MOLECULE TYPE: DNA (genomic)

( i x ) FEATURE:
( A ) NAME/KEY: CDS
( B ) LOCATION: 1..825

( x ) PUBLICATION INFORMATION:
( H ) DOCUMENT NUMBER: WO 94/12648
( I ) FILING DATE: 25-NOV-1993
( J ) PUBLICATION DATE: 09-JUN- 1994

( x i ) SEQUENCE DESCRIPTION: SEQ ID NO:18:

ATG CTG TCA CTG CTC CAC GCA TCA ACG CTG GCA GTC CTT GGG GCT CTG 48
Met Leu Ser Leu Leu His Ala Ser Thr Leu Ala Val Leu Gly Ala Leu
1 5 10 15

TGT GTA TAT GGT GCA GGT CAC CTA GAG CAA CCT CAA ATT TCC AGT ACT 96
Cys Val Tyr Gly Ala Gly His Leu Glu Gln Pro Gln Ile Ser Ser Thr
20 25 30

AAA ACG CTG TCA AAA ACA GCC CGC CTG GAA TGT GTG GTG TCT GGA ATA 144
Lys Thr Leu Ser Lys Thr Ala Arg Leu Glu Cys Val Val Ser Gly Ile
35 40 45

ACA ATT TCT GCA ACA TCT GTA TAT TGG TAT CGA GAG AGA CCT GGT GAA 192
Thr Ile Ser Ala Thr Ser Val Tyr Trp Tyr Arg Glu Arg Pro Gly Glu
50 55 60

GTC ATA CAG TTC CTG GTG TCC ATT TCA TAT GAC GGC ACT GTC AGA AAG 240
Val Ile Gln Phe Leu Val Ser Ile Ser Tyr Asp Gly Thr Val Arg Lys
65 70 75 80

GAA TCC GGC ATT CCG TCA GGC AAA TTT GAG GTG GAT AGG ATA CCT GAA 288
Glu Ser Gly Ile Pro Ser Gly Lys Phe Glu Val Asp Arg Ile Pro Glu
85 90 95

ACG TCT ACA TCC ACT CTC ACC ATT CAC AAT GTA GAG AAA CAG GAC ATA 336
Thr Ser Thr Ser Thr Leu Thr Ile His Asn Val Glu Lys Gln Asp Ile
100 105 110

GCT ACC TAC TAC TGT GCC TTG TGG GAG GCC CAG CAA GAG TTG GGC AAA 384
Ala Thr Tyr Tyr Cys Ala Leu Trp Glu Ala Gln Gln Glu Leu Gly Lys
115 120 125

AAA ATC AAG GTA TTT GGT CCC GGA ACA AAG CTT ATC ATT ACA GAT AAA 432
Lys Ile Lys Val Phe Gly Pro Gly Thr Lys Leu Ile Ile Thr Asp Lys
130 135 140

CAA CTT GAT GCA GAT GTT TCC CCC AAG CCC ACT ATT TTT CTT CCT TCA 480
Gln Leu Asp Ala Asp Val Ser Pro Lys Pro Thr Ile Phe Leu Pro Ser
145 150 155 160

ATT GCT GAA ACA AAG CTC CAG AAG GCT GGA ACA TAC CTT TGT CTT CTT 528
Ile Ala Glu Thr Lys Leu Gln Lys Ala Gly Thr Tyr Leu Cys Leu Leu
165 170 175

GAG AAA TTT TTC CCT GAT GTT ATT AAG ATA CAT TGG GAA GAA AAG AAG 576
Glu Lys Phe Phe Pro Asp Val Ile Lys Ile His Trp Glu Glu Lys Lys
180 185 190

AGC AAC ACG ATT CTG GGA TCC CAG GAG GGG AAC ACC ATG AAG ACT AAT 624
Ser Asn Thr Ile Leu Gly Ser Gln Glu Gly Asn Thr Met Lys Thr Asn
195 200 205

GAC ACA TAC ATG AAA TTT AGC TGG TTA ACG GTG CCA GAA AAG TCA CTG 672
Asp Thr Tyr Met Lys Phe Ser Trp Leu Thr Val Pro Glu Lys Ser Leu
210 215 220

GAC AAA GAA CAC AGA TGT ATC GTC AGA CAT GAG AAT AAT AAA AAC GGA 720
Asp Lys Glu His Arg Cys Ile Val Arg His Glu Asn Asn Lys Asn Gly
225 230 235 240

GTT GAT CAA GAA ATT ATC TTT CCT CCA ATA AAG ACA GAT GTC ATC ACA 768
Val Asp Gln Glu Ile Ile Phe Pro Pro Ile Lys Thr Asp Val Ile Thr
245 250 255

ATG GAT CCC AAA GAC AAT TGT TCA AAA GAT GCA AAT GAT ACA CTA CTG 816
Met Asp Pro Lys Asp Asn Cys Ser Lys Asp Ala Asn Asp Thr Leu Leu

-continued

```
                260                       265                       270

CTG CAG TAA                                                                    825
Leu Gln
        275
```

( 2 ) INFORMATION FOR SEQ ID NO:19:

( i ) SEQUENCE CHARACTERISTICS:
( A ) LENGTH: 274 amino acids
( B ) TYPE: amino acid
( D ) TOPOLOGY: linear ( i i ) MOLECULE TYPE: protein ( x i ) SEQUENCE DESCRIPTION: SEQ ID NO:19:

```
Met Leu Ser Leu Leu His Ala Ser Thr Leu Ala Val Leu Gly Ala Leu
  1               5                  10                  15

Cys Val Tyr Gly Ala Gly His Leu Glu Gln Pro Gln Ile Ser Ser Thr
             20                  25                  30

Lys Thr Leu Ser Lys Thr Ala Arg Leu Glu Cys Val Val Ser Gly Ile
         35                  40                  45

Thr Ile Ser Ala Thr Ser Val Tyr Trp Tyr Arg Glu Arg Pro Gly Glu
     50                  55                  60

Val Ile Gln Phe Leu Val Ser Ile Ser Tyr Asp Gly Thr Val Arg Lys
 65                  70                  75                  80

Glu Ser Gly Ile Pro Ser Gly Lys Phe Glu Val Asp Arg Ile Pro Glu
                 85                  90                  95

Thr Ser Thr Ser Thr Leu Thr Ile His Asn Val Glu Lys Gln Asp Ile
            100                 105                 110

Ala Thr Tyr Tyr Cys Ala Leu Trp Glu Ala Gln Gln Glu Leu Gly Lys
        115                 120                 125

Lys Ile Lys Val Phe Gly Pro Gly Thr Lys Leu Ile Ile Thr Asp Lys
    130                 135                 140

Gln Leu Asp Ala Asp Val Ser Pro Lys Pro Thr Ile Phe Leu Pro Ser
145                 150                 155                 160

Ile Ala Glu Thr Lys Leu Gln Lys Ala Gly Thr Tyr Leu Cys Leu Leu
                165                 170                 175

Glu Lys Phe Phe Pro Asp Val Ile Lys Ile His Trp Glu Glu Lys Lys
            180                 185                 190

Ser Asn Thr Ile Leu Gly Ser Gln Glu Gly Asn Thr Met Lys Thr Asn
        195                 200                 205

Asp Thr Tyr Met Lys Phe Ser Trp Leu Thr Val Pro Glu Lys Ser Leu
    210                 215                 220

Asp Lys Glu His Arg Cys Ile Val Arg His Glu Asn Asn Lys Asn Gly
225                 230                 235                 240

Val Asp Gln Glu Ile Ile Phe Pro Pro Ile Lys Thr Asp Val Ile Thr
                245                 250                 255

Met Asp Pro Lys Asp Asn Cys Ser Lys Asp Ala Asn Asp Thr Leu Leu
            260                 265                 270

Leu Gln
```

PRODUCTION OF SUBUNITS OF SOLUBLE T CELL RECEPTORS BY CO-TRANSFECTION

BACKGROUND OF THE INVENTION

1. Field of the Invention

The present invention relates to soluble T receptors and more particularly to secreted forms of soluble T receptors (sTR) VαC/α/VβC/β, VγCγ/VδCδ or VαCδ/VβC/γ and to their diagnostic and therapeutic applications.

2. Description of the Related Art

T lymphocytes are capable of recognizing, in a highly specific manner, myriads of antigens (Ag); this is by means of extremely diverse surface structures belonging to the superfamily of immunoglobulins (Ig), the T receptors (TR).

In man and in mice, most T lymphocytes in adults express sTR consisting of 2 variable glycoprotein sub-units called α and β. Like the Ig heavy and light chains, these subunits contain an amino-terminal variable (V) domain and a carboxy-terminal constant (C) domain and are, in addition, very generally covalently associated with each other via an interchain disulphide bridge. The nature of the antigens recognized by the αβ T receptor is relatively well established: they are complexes formed by an oligopeptide antigen (derived from the intracellular degradation of endogenous or exogenous proteins) closely associated with the polymorphic gene products situated in the so-called class I or II major histocompatibility complex (MHC). The interaction between the αβ T receptor and the MHC/Ag complexes is conventionally reinforced by so-called coreceptor or accessory molecules (CD4 and CD8), which recognize conserved portions of the class II and I MHC molecules respectively.

Another subpopulation of T lymphocytes which can be distinguished by the nature of the genes (γ and δ) encoding these T receptors has more recently been described. Contrary to the αβ T lymphocytes, the antigenic specificity of the γδ T cells still remains unclear. Based on the relative homology of the primary sequences of the αβ and γδ chains of the T receptor, some have predicted a structural similarity of the ligands for these receptors. In agreement with this hypothesis, a fraction of the γδ T lymphocytes was found to be directed against molecules structurally similar or identical to the products of the MHC conventionally recognized by the αβ T lymphocytes. However, there are also several examples of recognition by this T subpopulation of molecules of more distant structure, such as stress proteins or certain activating molecules such as CD48.

The present inventors have sought to generate "soluble" (secreted) forms of the γδ T receptor, which could be used (like the Ig's) as probes permitting the isolation, localization and possibly the purification of specific ligands.

Moreover, such soluble T receptors also have a number of clinical applications. Traunecker et al. (1989. Inunuol. Today 10:29) have reported attempts to produce soluble T receptors which consisted in removing the transmembrane (TM) portion of the α chains or β chains by introducing a translational termination codon upstream of the sequences encoding the TM region which proved unsuccessful, no secretion having been detected.

Following these initial failures, other strategies were then adopted. In most cases, the principle consisted in constructing chimetic proteins comprising the V, or V and C regions of the α and β subunits, joined to the C regions of immunoglobulins or to anchors of the glycosyl phosphatidylinositol (GPI) type. In the case of the TR/Ig fusion proteins, the main problem proved to be the sometimes predominant secretion of monomeric or homodimeric forms. In addition, the αβ sTR heterodimeric forms sometimes exhibited significant structural differences with the membrane forms; in particular, the 2 α and β chains were very generally non-covalently associated. This could consequently have effects on the overall structure and the fine antigenic specificity of such chimeric molecules. In the case of "lipidated" T receptors (anchored to the membrane by a GPI sequence), a sometimes quite high proportion of covalently associated αβ heterodimers could be obtained. However, the main disadvantage of this technique was the need for an enzymatic treatment (with phospholipase C), in order to liberate the T receptors in the medium, and therefore a production which is costly and of low yield. A procedure for producing so-called monochain T receptors, consisting in joining a Vα domain to a Vβ domain via a peptide bridge, has been proposed more recently. However, the use of this technique proved to be delicate. In particular, it assumed the introduction of a large number of mutations in certain hydrophobic zones of the V regions normally masked on the native protein, in order to render these monochain T receptors hydrosoluble.

All the examples of the production of soluble forms of T receptors described in the literature, in all cases in hybrid form, have shown an extreme variability of efficiency from one chain combination to another.

SUMMARY OF THE INVENTION

The present inventors have discovered that soluble T receptors could be easily obtained and with a high yield, regardless of the combination of chains used, by means of a process consisting in producing DNA molecules encoding each of the constituent T receptor submits from which the transmembrane portion has been deleted, and in co-transfecting these DNAs into a host cell.

The subject of the present invention is also a process for producing soluble T receptors, wherein the DNA sequences encoding each of the constituent T receptor submits, from which the transmembrane portion of the T receptor has been deleted, are co-transfected into a host cell.

According to the invention, VαC/α/VβCβ soluble T receptors are produced by co-transfecting, into a host cell, DNA sequences encoding the α and β submits of the Tαβ receptor from which the transmembrane portion of the Tαβ receptor has been deleted.

VγCγ/VδCδ soluble T receptors are also produced by co-transfecting, into a host cell, DNA sequences encoding the γ and δ submits of the Tγδ receptor from which the transmembrane portion of the Tγδ receptor has been deleted.

VαCγ/VβCδ and VαCδ/VβC/γ heterodimeric soluble T receptors are further produced, in which the constituent subunits are associated via a covalent bond, by co-transfecting, into a host cell, DNA sequences encoding the Cγ and Cδ domains of the γ and δ subunits of the Tγδ receptor from which their transmembrane portion has been deleted, fused respectively to the DNA sequences encoding the Vα and Vβ domains of the α and β subunits of the Tαβ receptor in order to obtain VαCγ/VβCδ receptors, or fused respectively to DNA sequences encoding the Vβ and Vα domains of the β and α subunits of the Tαβ receptor in order to obtain VαCδ/VβCδ receptors.

VγCγ/VαCδ hybrid soluble T receptors are also produced by co-transfecting, into a host cell, DNA sequences encoding the γ subunit of the Tγδ receptor from which its transmembrane portion has been deleted, with the DNA sequences encoding the Cδ domain of the δ subunit fused to the DNA sequences encoding the Vα domain of the α subunit of the Tαβ receptor. This construction is particularly advantageous and is based on the fact that certain Vα genes can be used either by αβ clones, or by γδ clones.

Advantageously, the DNA sequences of the Vδ2 and Vγ9 genes are used, for the constructions of the soluble T receptors of the invention, for the variable parts.

It may however be advantageous to produce VγC/65 /VδCδ receptors using a Vγ9 DNA sequence on the one hand, and by replacing the Vδ2 DNA sequence by other Vδ DNA sequences for the same reasons as those mentioned above for the construction of the VγCγ/VαCδ hybrid receptor. This construction makes it possible to obtain anti-α antibodies, or antibodies directed against Vδ's distinct from Vδ2.

Conversely, it is also possible to conserve the Vδ2 DNA and to replace the Vγ9 DNA sequence with other Vγ DNA sequences, in order to obtain anti-Vγ antibodies.

The invention also encompasses these embodiments of VγCγ/VδCδ soluble T receptors.

It should be noted that several Vδ segments (especially Vδ1) can be considered as Vα's, in the sense that they can be equally used by the α or δ chains of the T receptor. Thus, it can be considered that the examples of receptors produced in soluble form, which are provided here, demonstrate especially the usefulness of the process within the framework of the generation of monoclonal antibodies directed not only against the γ and δ, but also α, variable regions.

Advantageously, the deletion of the transmembrane portion of the constituent T receptor submits is carried out by introducing a translational termination codon upstream of the sequences encoding the transmembrane portion of these submits, especially by P.C.R. (Polymerase Chain Reaction) directed mutagenesis.

The DNA sequences are genomic DNA or cDNA sequences.

Preferably, the co-transfection is carried out into eukaryotic cells, especially hamster ovary cells (CEO).

The subject of the invention is also a fusion protein formed between a soluble T receptor and a peptide sequence, the peptide sequence being constitutive of a peptide or of a protein, the fusion protein being obtained by fusing the DNA sequence encoding the peptide or the protein to one of the chains or to the two chains of DNA encoding the submits of a T receptor from which their transmembrane portion has been deleted, followed by a co-transfection of the DNA sequences thus fused into a host cell.

Advantageously in this case, the peptide sequence is that of interleukin-2 (IL-2).

The subject of the invention is also human or animal polyclonal or monoclonal antibodies directed against a soluble T receptor obtained by the process of the invention or an sTR-IL2 fusion protein as defined above.

The monoclonal antibodies according to the invention can be prepared according to a conventional technique. To this effect, the soluble T receptors, optionally fused with interleukin-2 or another protein, can be coupled if necessary to an immunogenic agent, such as tetanus toxoid, via a coupling agent such as a his diazotized benzidine.

The present invention also encompasses the fragments and the derivatives of monoclonal antibodies according to the invention. These fragments are especially $F(ab')_2$ fragments which can be obtained by enzymatic cleavage of the antibody molecules with pepsin, the Fab' fragments which can be obtained by reducing the disulphide bridges of the $F(ab')_2$ fragments and the Fab fragments which can be obtained by enzymatic cleavage of the antibody molecules with papain in the presence of a reducing agent. These fragments, as well as the Fc fragments, can also be obtained by genetic engineering.

The derivatives of monoclonal antibodies are for example antibodies or fragments of these antibodies to which markers such as a radioisotope are linked. The derivatives of monoclonal antibodies are also antibodies or fragments of these antibodies to which therapeutically active molecules are linked.

The subject of the invention is also hybridomas producing monoclonal antibodies specific for the peptide sequence described above. These hybridomas can be obtained by the conventional techniques of cell fusion between spleen cells activated in vitro by the antigen or obtained from an animal immunized against the peptide sequence of the invention, and cells from a myelomatous line.

The subject of the invention is also a diagnostic composition comprising a soluble T receptor obtained by a process according to the invention or an sTR-peptide sequence, especially sTR-IL2, fusion protein as defined above, or alternatively a monoclonal antibody according to the invention.

The diagnostic composition according to the invention can be used for the typing of cellular specificities linked to the T receptor. Indeed, a soluble T receptor can be used as such. However, because of the probably weak affinity of the latter for its specific ligand, it is advantageous to couple the soluble T receptors to a support, in order to increase their avidity by increasing their valency.

The support may consist of any support traditionally used, such as organic or magnetic beads.

Such supports are for example plastic plates used for the ELISA tests on which the soluble T receptor is attached in the same manner as immunoglobulins, tosyl-activated magnetic beads, for example those marketed by Dynal, Oslo, Norway, or alternatively AFFIGEL type activated gels such as those marketed by BIORAD.

The coupling techniques are those conventionally used and indicated by the distributor for the supports commercially available.

These methods may consist in a chemical coupling or by means of monoclonal antibodies directed against the soluble T receptors in question, the latter being themselves coupled to the support by chemical coupling.

Advantageously, the diagnostic compositions comprise a fused protein as described above, consisting of a soluble T receptor and an antigenic determinant against which specific antibodies are available.

Such diagnostic compositions can be used for the typing of cellular specificities not detected by conventional serological techniques.

The diagnostic composition according to the invention may also comprise monoclonal antibodies as defined above, and preferably a panel of monoclonal antibodies directed against the V and C portions of the chains of the T receptors obtained by immunizing animals against the soluble T receptors obtained according to the invention, previously purified.

In order to improve the efficacy of the immunizations, it is also possible to inject sTR-IL2 fusion proteins as defined above.

Such a diagnostic composition can be used especially for the detection of mono- or oligoclonal proliferations, such as those encountered in T leukaemias for example.

According to the invention, the diagnostic composition is brought into contact with a biological sample, for example a blood sample containing pathological T lymphocytes, and the complex formed with the ligand specific for the T receptor and the soluble T receptor or the fusion protein comprising the soluble T receptor and an antigenie determinant or the complex formed by the monoclonal antibodies according to the invention and the soluble T receptor or the soluble T receptor-IL2 fusion protein against which they are specifically directed, is detected.

These processes can be based on an RIA, RIPA or IRMA type radioimmunological method, or an immuno-enzymatic method of the WESTERN-BLOT type on strips or of the ELISA type.

For the implementation of these processes of detection, unlabelled cold molecules or molecules labelled by means of a suitable marker which may be biotin or its derivatives, an enzyme such as peroxidase, a fluorescent marker such as fluorescein, a radioactive marker and the like, are used.

These in vitro diagnostic processes comprise for example the following steps:

- depositing a determined quantity of a composition containing a soluble T receptor, a soluble receptor fused with an antigenie determinant or a monoclonal antibody according to the invention directed against the soluble T receptor or the soluble T receptor-Interleukin 2 fusion protein according to the invention, in the wells of a microtitre plate or on another support such as beads or a nitrocellulose membrane,
- depositing, in the wells, the biological sample to be tested, or incubating the latter with the beads or the membrane, in the presence of saturating agents or after prior saturation of the activated supports,
- after incubating and rinsing the microplates or the beads, depositing in the wells or incubating with the beads a system for revealing the soluble T receptor-ligand complex which may have formed.

The kits for implementing the diagnostic process of the invention comprise:

- at least one diagnostic composition according to the invention,
- reagents for preparing a medium suitable for producing a complex between the ligand(s) which may be present in a biological sample,
- one or more optionally labelled reagents capable of reacting with the complex formed.

The subject of the invention is also a therapeutic composition characterized in that it comprises a soluble T receptor obtained according to the process of the invention or a fusion protein as defined above, especially an sTR-IL2 according to the invention.

Such a therapeutic composition is useful especially in the treatment of pathological processes in which a pauciclonal proliferation of T lymphocytes is observed, such as T leukaemias or lymphomas and certain autoimmune diseases.

It is preferably administered by injection in an appropriate vehicle.

The administration of this therapeutic composition has a double purpose. It permits, on the one hand, the induction of an anti-idiotypic immuno response, resulting, in this case, in the active and selective removal of the cells carrying these idiotypes, and, on the other hand, the blocking, by competition, of the recognition of autologous antigens in the case of auto-immune proliferations.

Advantageously, the therapeutic composition according to the invention comprises a heterodimeric soluble T receptor as defined above, optionally carried by a fusion protein.

The therapeutic composition according to the invention may also comprise a monoclonal antibody according to the invention, optionally coupled to a therapeutically active molecule, for example a cytotoxic molecule, or a monoclonal antibody fragment or derivative as defined above.

Such a composition permits the direct removal of mono- or oligoclonal cells encountered in certain types of T leukaemias.

BRIEF DESCRIPTION OF THE DRAWINGS

The production of soluble T receptors in the case of TRγδ will be described in detail below with reference to the accompanying figures in which:

FIG. 1 shows the sequences SEQ ID NO:1–SEQ ID NO:15 as depicted on the attached sequence listing.

FIGS. 2A and 2B represent the corresponding nucleotide and peptide sequences of the soluble δ and γ chains of the clone used for the construction of the soluble T receptor described above. In particular, FIG. 2A shows the sequences SEQ ID NO:16 and SEQ ID NO:17 and FIG. 2B shows the sequences SEQ ID NO: 18 and SEQ ID NO:19 as depicted on the attached sequence listing.

SN represents the supernatant from the culture of the CHO cells, transfected with a non-pertinent cDNA (C) or with the cDNAs of the soluble γ and δ subunits according to the invention (sγδ).

The monoclonal antibodies giving a significant radioimmunological signal are represented as bold rectangles.

Figure 4:
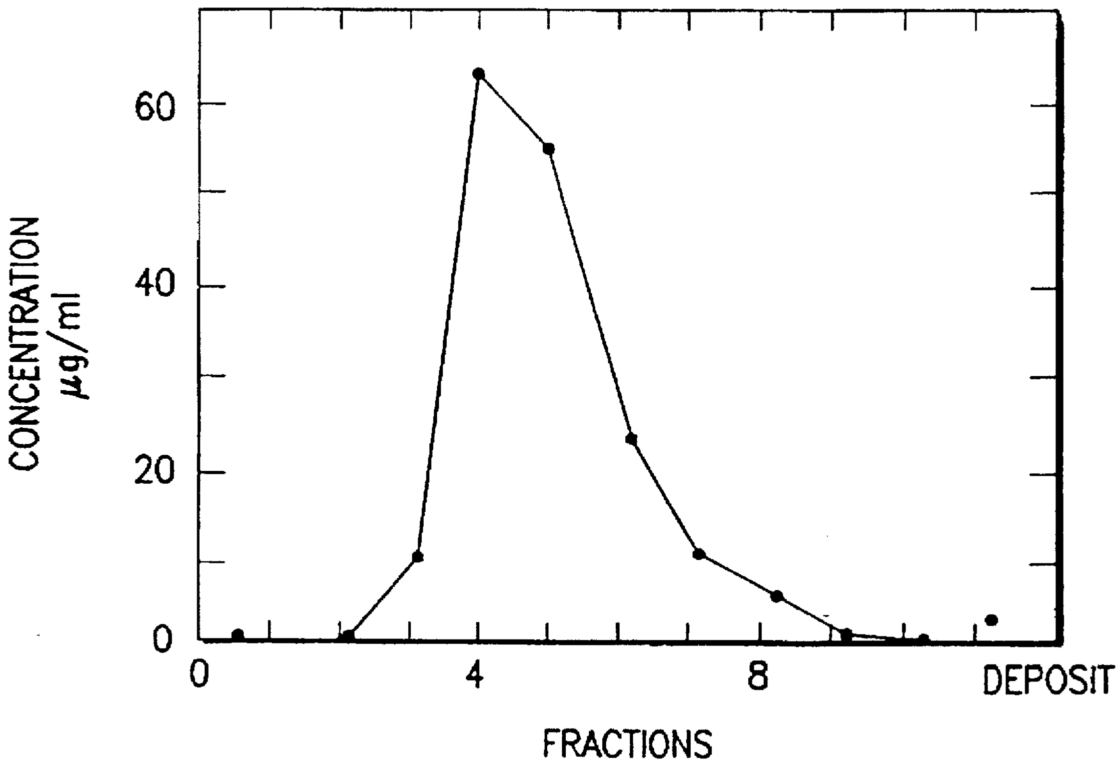

FIG. 4 represents the titration in soluble TR activity expressed in μg/ml, as attested by the IRMA test (sandwich 7B6/TiVδ2), of the fractions eluted from an affinity column coupled with the anti-Vγ 7B6 antibody (marketed by Immunotech), onto which have been applied about 500 ml of supernatant from the culture of γδsFS-CHO cells.

Figure 5:
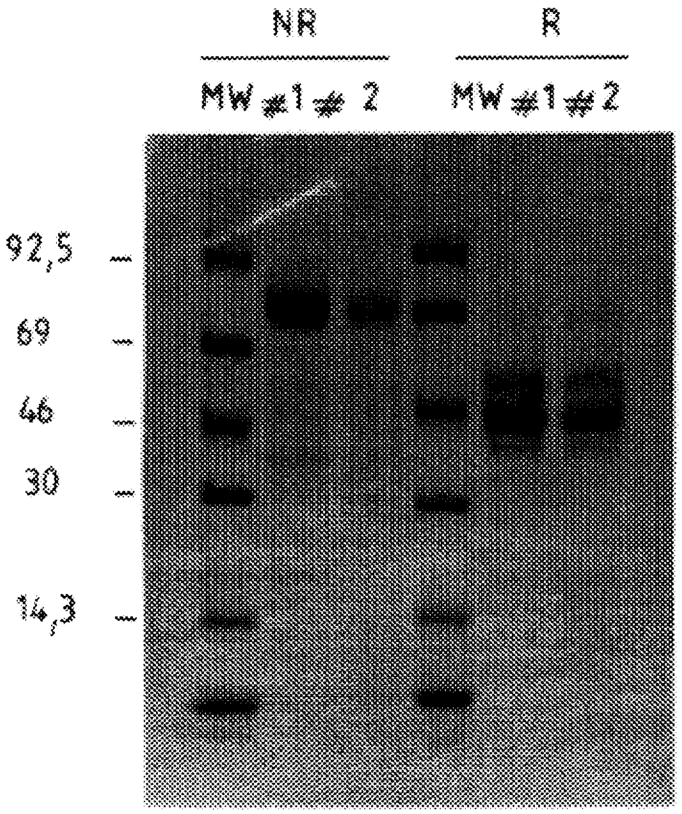

FIG. 5 represents the SDS-PAGE analysis of fractions positive for the soluble TR activity, as attested by the IRMA test (sandwich 7B6/TiVδ2), of the fractions eluted from an affinity column coupled with the anti-Vγ9B6 antibody.

Two independent preparations (#1 and #2) were analysed under non-reducing (on the left) and reducing (on the right) conditions. MW=molecular weight markers.

DETAILED DESCRIPTION OF THE PREFERRED EMBODIMENTS

EXAMPLE 1

1. Construction And Expression of the γδs Genes For the sTRs

The γδs G 115 human lymphocyte clone (whose nucleotide and peptide sequences corresponding to the soluble δ and γ chains are represented in FIG. 2, in A and B respectively) expressing T V9JPCIγ/V2D3J1Cδ receptors was used for the construction of the γδs genes and the expression of the soluble T receptors.

This clone was used for several reasons of which the main ones are:

- the great majority of the γδ T receptors of peripheral blood human leucocytes comprise similar V(D)J regions such that the structural and functional results obtained with the soluble form of the specific TR used can be easily applied to the TR expressed by a large proportion of γδ cells,
- monoclonal antibodies specific for the Cγ, Cδ, Vγ9 and Vδ2 regions are easily available and can be used to monitor the production and the purification of the soluble TR molecules,
- unlike most γδ Vδ1-positive human T lymphocytes, the γ and δ chains of the T receptors of the G 115 clone are covalently linked by a disulphide bridge which highly stabilizes the molecule after its secretion into the medium,
- the antigenic specificity of the G 115 clone is fairly well known. In particular, this clone kills the cells of a Burkitt's lymphoma (called Dadi) and also recognizes an antigen present in water-soluble extracts of *Mycobacterium tuberculosis*.

The G 115 clone, obtained from Tγδ lymphocytes derived from human peripheral blood leucocytes, was maintained in an RPMI 1640 medium containing 8% human serum, 2 mM L-glutamin and 150 BRMP (Biological Response Modifier Program) units of IL2 and stimulated for one week out of two with 0.5 μg/ml of leucoagglutinin (Pharmacia, France), irradiated peripheral blood leucocytes and irradiated and EBV-transformed B lymphoblasts.

Figure 1A:
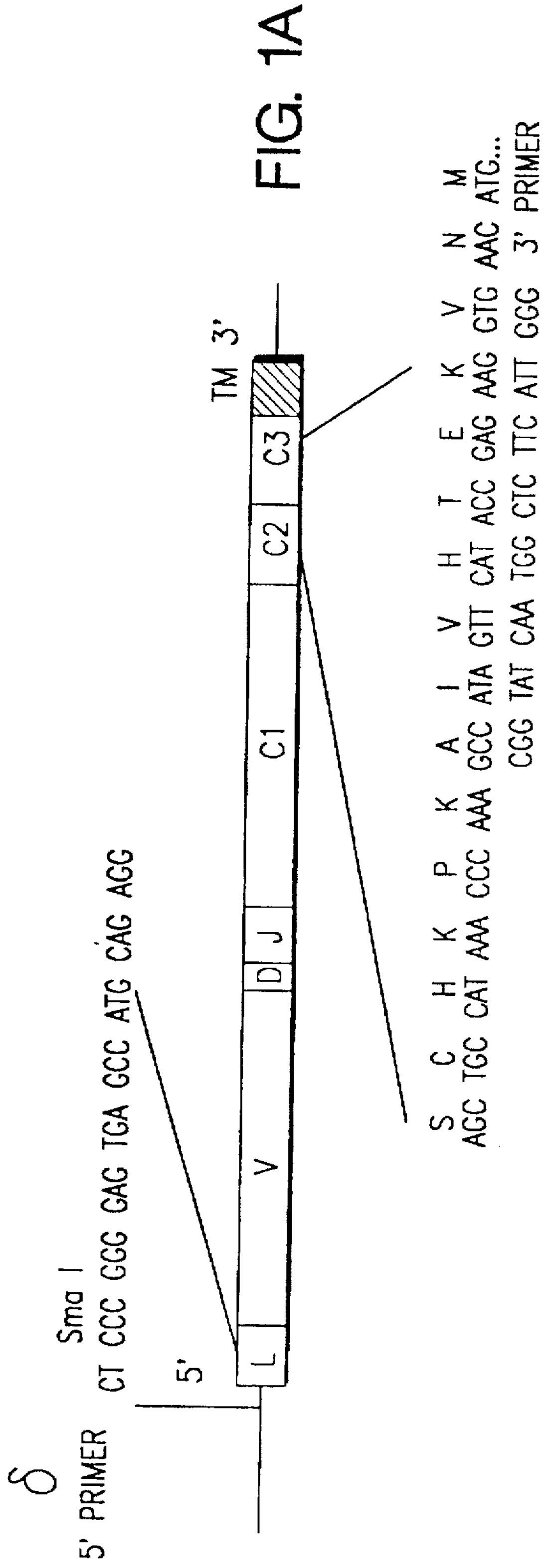
FIGS. 1 and 1B represent products of assembly of the γ and δ genes. The sequences of the 5' and 3' primers used to amplify the cDNAs permitting the production of the soluble Tγδ receptors (γs and δs cDNA) are represented above and below the γ and δ cDNAs respectively. The positions of the termination codons are represented in bold characters. The grey parts in 3' of the γ and δ cDNAs correspond to the hydrophobic transmembrane (TM) regions.
Figure 1B:
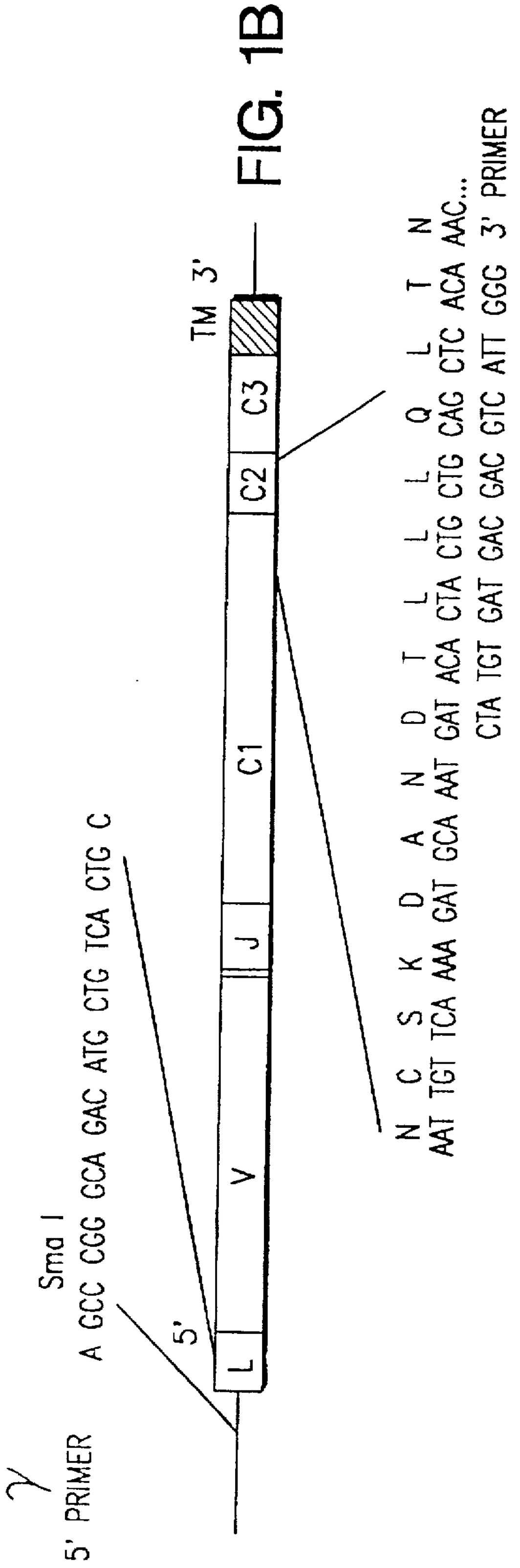

After two washes in phosphate buffered saline solution, $5\times10^6$ cells were lysed on ice in a Tris-HCl buffer (80 mM, pH 7.5) containing 100 mMNaCl, 5 mM EDTA and 0.5% by weight of Triton X100. After centrifuging, the supernatant was harvested and mixed with an equal volume of phenol at 65° C. The RNA was extracted by a phenol/CHCl₃ treatment, precipitated in 2.5 volumes of ethanol and solubilized in 40 μl of 10 mM Tris/1 mM EDTA). 5 μl of total RNA were reverse-transcribed for 1 hour at 37° C. by means of a 3'-phosphated primer containing translational termination codons upstream of the hydrophobic transmembrane region of the γ and δ genes, after the $Lys^{247}$ and $Gln^{274}$ codons, as represented in FIG. 1, at a concentration of 50 pM, the four dNTPs at a concentration of 1 mM each and 200 units of mouse mammary tumor virus reverse transcriptase (MMTV) (Boehringer Mannheim, Germany), in a final volume of 25 μl. 1.75 μl of a mixture for PCR (containing 13 mM Tris-HCl (pH 8.2), 66 mM KCl, 2 mM MgCl₂, 2 U of Taq polymerase (Boehringer) and 50 pM of 5'-phosphated primer represented in FIG. 1 were added to the material obtained by reverse transcription and 30 amplification cycles (94° C.—1 min, 45° C.—1 min, 72° C.—1 min) were carried out. The amplified DNA was purified after electrophoresis on a low melting point agarose gel and cloned into a plasmid Bluescript SK+ (Stratagene, La Jolla, Calif.) digested with SmaI. The sequencing was carried out using a system of double-stranded template according to the procedure provided by the supplier of the USB Sequenase kit. The fragments were cloned into an expression vector pKCR6 (Matrisian et al., Proc. Natl. Acad. Sci. USA. 83:9413) digested with EcoRI.

The plasmid DNA was then introduced into DHFR (dihydrofolate reductase)-negative hamster ovary cells DUKX-B11, cultured in RPMI 1640 medium, supplemented with 8% foetal calf serum, 2 mM L-glutamin, thymidin, adenosin and deoxyadenosin at 10 μg/ml each, by the calciumphosphate precipitation technique (Wiglet et al., 1979 Cell. 16:777). The DHFR-positive cells were selected by culturing the transfected cells for three weeks in RPMI medium, supplemented with foetal calf serum and n-glutamin (2 mM) without nucleosides. The stable transfectants were then cloned by the limiting dilution technique.

2. Detection, Purification And Characterization of the Soluble Tγδ Receptors a) Detection of the soluble T receptors The monoclonal antibodies used for the detection of the soluble TRs were labelled with $^{125}I$ by the Iodogen method (Fraker et al., 1978, Biochem.-Biophys. Res. Commun. 80:849). The T receptors were detected by a sandwich immunoradiometric assay (IRMA) by means of pairs of monoclonal antibodies specific for the γ and δ chains.

Immulon-1 microtitre plates (Dynatech, Marnes, France) were coated for 90 min at 37° C. with 50 μl of Y102 (or 7B6) monoclonal antibody at 40 μg/ml in a phosphate buffered saline solution. After removal of the antibody, the unbound sites were saturated with a phosphate buffered saline solution containing 0.5% bovine serum albumin for 1 hour at room temperature. The samples to be analysed were then added in an amount of 40 μl at the same time as 10 μl of labelled TiVδ2 monoclonal antibody. After incubating for 90 min at 37° C., the wells were rinsed four times with 100 μl of a phosphate buffered saline solution supplemented with bovine serum albumin.

The bound radioactivity was measured in a γ scintillation counter. The following set of antibodies was used to measure the secretion of soluble TRγδ by the IRMA technique: anti-Vγ9 (Y102, B37, 7B6), anti-Cγ (B121) and anti-Vδ2 (TiVδ2) antibodies (Miossec et al., 1989, J. Exp. Med. 171:1171). A monoclonal antibody specific for IL2 was also used as negative control.

Figure 3:
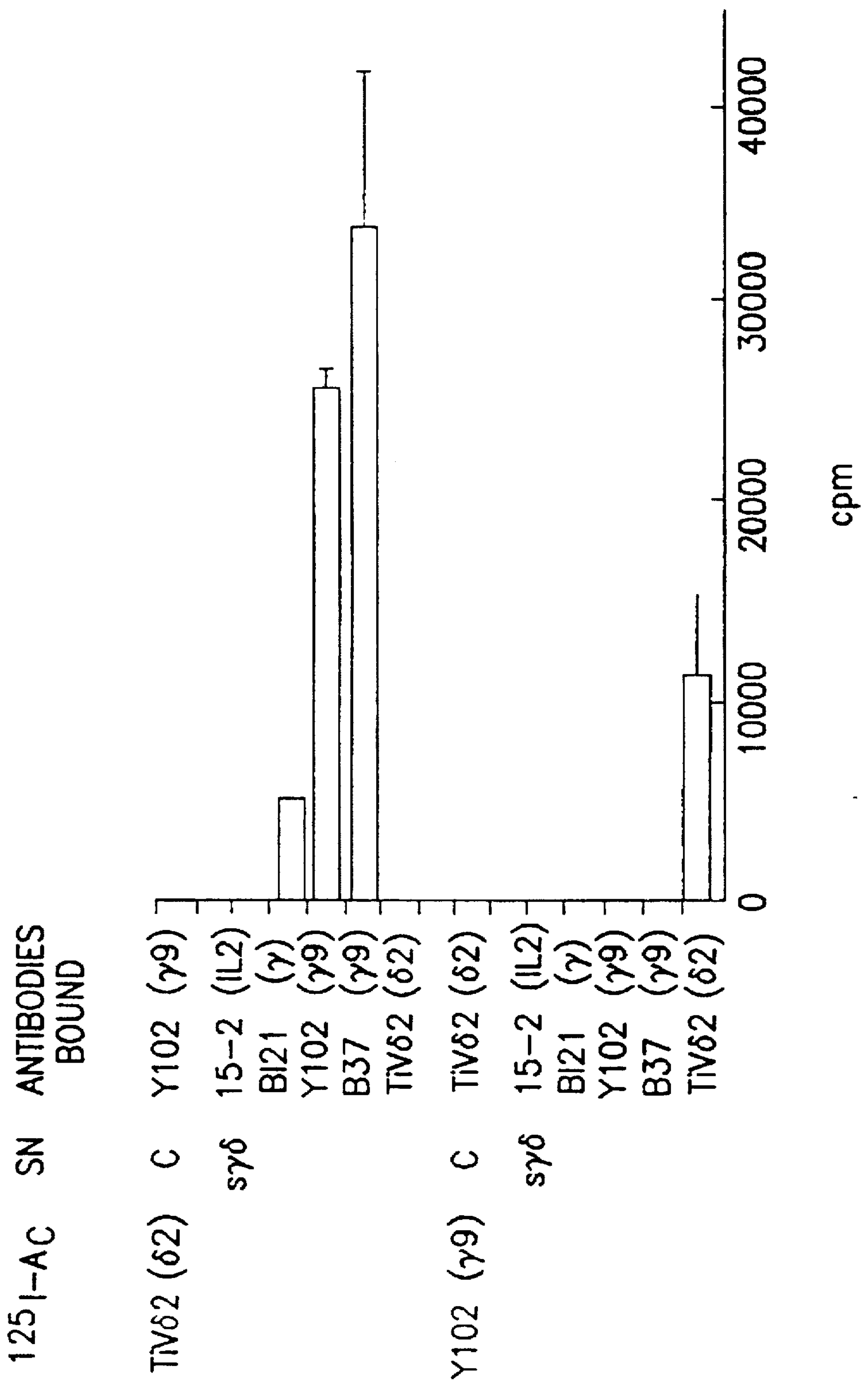
FIG. 3 represents the results of the tests for detection of sTRγδ by the IRMA technique in medium packaged from CHO cells transfected with γs/δs.

With the various combinations of antibodies, no signal was observed with the supernatants of non-transfected hamster ovary cells (CHO), of cells transletted with a nonpertinent cDNA or of cells transfected either with a truncated γs cDNA or a truncated δs cDNA (FIG. 3). But the soluble γδ hetero-dimers were clearly detected by IRMA (radioimmunological assay) in the supernatants of CHO cells co-transfected with soluble γ and soluble δ assembly products (γδsFS-CHO) when pairs of antibodies specific for Vδ2/Cγ or Vδ2/Vγ9 were used (FIG. 3), which suggests that the soluble TR molecules secreted by the γδF5-CHO cells were predominantly heterodimers.

b) Purification of the soluble T receptors 10 mg of Y102 or 7B6 monoclonal antibody (anti-Vγ9) were covalently linked to a matrix of activated agarose beads (Affigel, Biorad, Richmond, Calif.) according to the instructions of the supplier.

The culture supernatants were applied to an affinity column at a rate of 30 ml/h at 4° C. After washing with a phosphate buffered saline solution, the bound material was eluted with a 0.2M glycine buffer (pH 2.5). The eluted fractions were neutralized all at once with 1M Na₂HPO₄.

The fractions positive for the soluble TR activity as attested by the IRMA test were combined, dialysed overnight against distilled water and concentrated by evaporation.

Soluble TR samples were prepared in a buffer for gel electrophoresis with or without reducing agent, separated by SDS-PAGE and transferred onto a nitro-cellulose membrane in accordance with the recommendations of the supplier. After saturating the unbound sites with a blocking buffer (dried skimmed milk and Tween 20), the fingerprints obtained were incubated in the presence of primary antibody (hybridoma supernatant diluted one-third with the blocking buffer) for 2 hours at room temperature. After washing, an anti-Ig-horseradish peroxidase conjugate was added, and the incubation continued for another 2 hours. The bound antibodies were revealed with diaminobenzidine (1 mg/ml), $H_2O_2$ and $CoCl_2$.

In a typical preparation, 3.3 mg (calculated using a coefficient for 1% extinction of 1.5, as calculated for the immunoglobulins) of affinity-purified γδ TRs were treated with Vibrio cholerae neuraminidase (Boehringer Mannheim) in 1 ml of buffer containing 50 mM sodium acetate, 150 mM NaCl and 4 mM $CaCl_2$ at pH 5.5 for 1 hour at 37° C.

Under these conditions, the reaction was estimated to be complete by determining control assays for digested samples by isoelectric focusing in IEF 3-9 PhastGel medium (Pharmacia).

After dilution with a 0.1M sodium phosphate buffer, pH 7.3, the sample was concentrated by means of a centripep column at 30,000 revolutions (Amicon) before protelysis.

The neuraminidase-treated γδ receptors were digested at 37° C. for 30 minutes with papain (Worthington) at an enzyme/substrate ratio of 1/500 in the presence of 1.5 mM 2-mercaptoethanol and 1.25 mM EDTA. The reaction was completed by addition of N-ethylmaleimide.

These conditions were sufficient to completely eliminate the interchain disulphide bridge as attested by SDS-PAGE analysis under non-reducing conditions. Higher enzyme/substrate ratios and/or longer incubation times provided no proof of an additional protein cleavage. The reaction medium was then applied to a Zorbax CF-250 size-exclusion chromatography column (DuPont - New England Nuclear) which made it possible to obtain, after elution, the T receptor treated with papain and neuraminidase in the form of a single peak at about 65 kDa compared with 75 kDa for the native protein. No sign of chain dissociation was apparent.

After concentrating on a centripep, the material described above was incubated overnight at 37° C. in the presence of endoglycosidase F and N-glycosidase F (Boehringer Mannhein) under non-denaturing conditions (0.1M sodium phosphate buffer, pH 7.3), as recommended by the manufacturer. A final purification was carried out by means of a Mono Q high-performance anion-exchange chromatography column (Pharmacia).

The total yield from 3.3 mg of affinity-purified T receptor was 1.1 mg or about 34%.

The material eluted from the anti-Vγ9 column consisted essentially of γδ heterodimers since it was precipitated by monoclonal antibodies specific for Vδ2. In addition, an SDS-PAGE analysis under reducing and non-reducing conditions showed that these heterodimers were linked by a covalent bond.

Indeed, under non-reducing conditions, a diffuse principal band having an apparent molecular weight of 75–80 kD was observed, which separated under reducing conditions into two predominant components of 42 and 44 kD and two minor components of 50 and 39 kD. Identical patterns were obtained with material precipitated in stages with anti-Vγ9 and anti-Vδ2 monoclonal antibodies. By means of monoclonal antibodies generated against this soluble receptor (monoclonal antibodies 360 and 389, cf. below), it was possible to show by the Western-blot technique that the 50 kD and 44 kD bands corresponded to the γ chain, and that the 42 and 39 kD band corresponded to the δ chain. The differences in the sizes of the soluble γ and δ species were due to the different degrees of N-glycosylation, as subsequently specified.

3. Production And Properties of Monoclonal Antibodies Directed Against the Soluble T Receptors of the Invention a) Generation of monoclonal antibodies directed against soluble forms of γδ TR after immunization of mice against soluble γδ TRs:

BALB/c mice were immunized with soluble γδ T receptors, in accordance with the following procedure: on day 1, 50 μg of protein in 500 μl of emulsified complete Freund's adjuvant at 50% in 0.9% NaCl were subcutaneously injected at four different points. On day 25, the same procedure was repeated in incomplete Freund's adjuvant. A booster was made by 3 intraperitoneal injections on days 50, 51 and 52, by means of 15 μg of protein each in 250 μl of 0.9% NaCl. Splenocytes harvested on day 53 were fused with X63 Ag 8653 myeloma. Hypoxanthine/aminopterin/thymidin-resistant colonies were screened by a radioimmunological assay (RIA) by means of an iodine-labelled soluble T receptor, in accordance with the IODOGEN method.

To this effect, 96-well microtitre plates coated with avidin (Immunotech) were incubated with biotinylated anti-mouse goat immunoglobulins (GAMIG, Immunotech) in PBS, BSA, $NaN_3$ overnight at 4° C., and then washed 3 times in Tween PBS. 100 μl ($10^5$ cpm) of radiolabelled soluble T receptors were incubated for 2 hours at room temperature and washed 3 times in PBS-Tween. The bound radiolabelled soluble T receptors were assayed by γ counting.

Nine monoclonal antibodies recognizing all or part of the human γδ T lymphocytes were obtained from an immunized mouse spleen, 2 anti-Vγ9 antibodies (292 and 360), 2 anti-Vδ2 antibodies (1 and 389), 1 γδ pan anti-body (510) and 4 antibodies directed against γδ sub-populations (49, 60, 103 and 515).

b) Reactivity of anti-soluble TR monoclonal antibodies towards mono- and polyclonal human lymphold lines:

Monoclonal antibodies having produced an RIA signal were then tested by immunofluorescence to determine their ability to recognize T receptors linked to the membranes of the G9 clone. The fine specificity of these monoclonal antibodies was finally studied by screening their reactivity towards T lymphocyte clones and lines whose T receptor phenotype was known.

From a single fusion experiment, the supernatants of 16 colonies (3% of the inoculated wells) gave a positive RIA signal and among them, eleven contained monoclonal antibodies recognizing the G9 clone in an indirect immunofluorescence assay. The specificity of 7 monoclonal antibodies was measured by flow cytometric analysis.

Three monoclonal antibodies (52, 106 and 510) were directed against a determinant which was common to all the Tγδ receptors but not to the Tαβ receptors. Two monoclonal antibodies (292 and 360) were specific for T receptors comprising the Vγ9 region and two monoclonal antibodies (1 and 389) for T receptors comprising the γδ2 region. No precise specificity could be attributed to the remaining monoclonal antibodies (49, 60, 103 and 515) which recognized subpopulations of γδ lymphocytes but whose reactivity could not be correlated with the presence of a particular V region of T receptor (Table I below).

It should be noted that all the monoclonal antibodies were capable of recognizing non-reduced soluble T receptors in Western-blot analyses, and several also reacted with γ or δ species isolated after reduction (Table II), unlike most V-specific monoclonal antibodies generated against native T receptors (linked to membranes). In agreement with attributions of specificity deduced from flow cytometric experiments, the monoclonal antibodies 389 and 360 recognized various species (molecular mass 39–42 kDa and 44–50 kDa, respectively), which could correspond to the δ and γ chains respectively. In addition, since the γδ52 and 510 pan monoclonal antibodies, and the antibody 389 specific for Vδ2 reacting with the same species of 39–42 kDa, this indicating that the monoclonal antibodies 52 and 510 were directed against the Cδ region (Table I).

In order to facilitate and to permit the oriented integration of the complementary DNAs encoding the soluble gamma and delta chains in the eukaryotic system expression vector pKCR6, a DNA fragment previously cloned between the XbaI and SalI sites of the vector pKCSRα was introduced between the KpnI sites of this vector.

The digestion of the vector pKCR6 thus modified by the XhoI and XbaI enzymes liberated these two sites and permitted an oriented cloning, the XhoI site being situated between 5' of the coding sequence and the XbaI site in 3'.

b) Generation of a complementary DNA encoding a soluble Vγ8 chain b1) PCR cloning of a soluble Vγ8 chain The RNA used for this cloning is obtained from a Tγδ clone.

TABLE 1

Circulating cytometric analysis of clones of Tγδ by means of an anti-sTR monoclonal antibody. The phenotype of the T lymphocyte clones was determined by labelling with Tiγa (anti-Bγ9), TiVδ2) and A13 (anti-Vδ1) antibodies; NR (not carried out).

| Clones | Vγ9 | Vδ2 | Vδ1 | 510 | 106 | 292 | 360 | 1 | 389 | 49 | 60 | 103 | 515 |
|---|---|---|---|---|---|---|---|---|---|---|---|---|---|
| G9 | + | + | − | + | + | + | + | + | + | + | + | + | + |
| M39 | + | + | − | + | NR | + | + | + | + | − | + | + | + |
| G12 | + | + | − | + | NR | + | + | + | + | − | + | + | + |
| Tγ3 | + | + | − | + | + | + | + | + | + | − | + | + | + |
| Tγ6 | + | + | − | + | + | + | + | + | + | − | + | + | + |
| Tγ11 | + | + | − | + | + | + | + | + | + | − | + | + | + |
| Tγ12 | + | + | − | + | + | + | + | + | + | − | + | + | + |
| Tγ15 | + | + | − | + | + | + | + | + | + | − | + | + | + |
| Tγ30 | + | + | − | + | + | + | + | + | + | − | + | + | + |
| G93 | + | + | − | + | + | + | + | + | + | − | − | − | − |
| T14 | − | + | − | + | NR | − | − | + | + | − | + | + | + |
| F11 | + | − | + | + | NR | + | + | − | − | − | − | − | − |
| M7 | − | − | + | + | NR | − | − | − | − | − | − | − | − |
| M8 | − | − | + | + | + | − | − | − | − | − | + | − | − |

TABLE II

Results of the Western-blot analyses of soluble T receptors by means of anti-sTR antibodies. The apparent molecular mass (in kDa) of the species recognized by each antibody is presented. (*NR = no reactivity; R = reactivity)

| Hybridoma | Western-blot analysis NR* | R* | Specificity |
|---|---|---|---|
| 52 | 80 | 39/42 | pan δ |
| 106 | 80 | — | pan γδ |
| 510 | 80 | 39/42 | pan δ |
| 1 | 80 | — | Vδ2 |
| 389 | 80 | 39/42 | Vδ2 |
| 292 | 80 | — | Vδ9 |
| 360 | 80 | 44/50 | Vδ9 |
| 49 | 80 | — | γδ subpopulations |
| 60 | 80 | — | γδ subpopulations |
| 103 | 80 | 39/42 | δ subpopulations |
| 515 | 80 | 39/42 | δ subpopulations |

EXAMPLE 2

1. Construction of Other γδ Soluble T Receptors

Other γδ soluble receptors were prepared as described below, after modification of the multiple cloning site of the expression vector pKCR6.

a) Modification of the multiple cloning site of the expression vector pKCR6

The oligonucleotide primer used for the synthesis of the first complementary DNA strand is the following:

5' GGG TTA CTG CAG CAG TAG TGT ATC 3' (SEQ ID NO:1)

The amplification of this cDNA was carried out by means of the oligonucleotide described above used as antisense primer and a sense primer containing a site for the XhoI restriction enzyme upstream of the translational initiation codon. The sequence of this oligonucleotide is the following:

5' CCC TCG AGA TGC TGT TGG CTC TAG CTC 3' (SEQ ID NO:2)

The DNA fragment obtained at the end of this amplification was cloned into the vector pBS-SK opened by the SmaI restriction enzyme and then sequenced. The sequence obtained is in conformity with that described in the literature (Cell. (1986) 45:237–246) with the exception of the joining sequence involving the Jγ1 segment:

Vγ8 N Jγ1 TGT GCC ACC TGG GAC AGT CAT TAT TAT AAG AAA CTC TTT (SEQ ID NO:3)

b2) Integration into the expression vector and transfection into eukaryotic cells The cDNA fragment encoding a soluble Vγ8 chain was extracted from the vector pBS-SK after digestion with the restriction enzymes XhoI and XbaI and integrated into the modified expression vector pKCR6 described in a) digested with the same enzymes.

The vector thus obtained was co-transfected in combination with the expression vector containing the cDNA encoding the soluble Vδ2 chain.

The procedure for transfection, screening of the producing clones and purification of the soluble TCRs produced is analogous to that described above for the production of soluble Vγ9 Vδ2 TCR.

c) Generation of a complementary DNA encoding a soluble Vδ3 chain cl) PCR cloning of a soluble Vδ3 chain The RNA used for this cloning is obtained from a Tγδ clone.

The nucleotide primer used for the synthesis of the first complementary DNA strand is the following:

5' GGG TTA CTT CTC GGT ATG AAC TAT GGC 3' (SEQ ID NO:4)

The amplification of this cDNA was carried out by means of the oligonucleotide described above used as antisense primer and a sense primer containing a site for the XhoI restriction enzyme upstream of the translational initiation codon. The sequence of this oligonucleotide is the following:

5' GAC TCG AGA AAA GAT GAT TCT TAC TGT GGG 3' (SEQ ID NO:5)

The DNA fragment obtained at the end of this amplification was cloned into the vector pBS-SK opened by the SmaI restriction enzyme and then sequenced. The sequence obtained is in conformity with that described in the literature (j. Exp. Med. (1989) 169:393–405) with the exception of the joining sequence involving the Dδ2, Dδ3 and Jδ1 segments:

Vδ3 N Dδ2 N Dδ3 ACT TAC TGT CCT T TT TCC CGG CTC T TG GGG G AC ACC Jδ1 GAT AAA (SEQ ID NO:6)

c2) Integration into the expression vector and transfection into eukaryotic cells The cDNA fragment encoding a soluble Vδ3 chain was extracted from the vector pBS-SK after digestion with the restriction enzymes XhoI and XbaI and integrated into the modified expression vector pKCR6 described in a) digested with the same enzymes.

The vector thus obtained was co-transfected in combination with the expression vector containing the cDNA encoding the soluble Vγ9 chain.

The procedure for transfection, screening of the producing clones and purification of the soluble TCRs produced is analogous to that described above for the production of soluble TCR Vγ9 Vδ2.

d) Generation of a complementary DNA encoding a soluble Vδ1 chain

The DNA complementary to a total Vδ1 Cδ chain cloned into the vector pBS-SK between the SalI and BamHI restriction sites was used.

This fragment was sequenced completely and exhibits no variation compared with the sequence described in the literature (Eur. J. Immunol. (1989) 19:1545–1549) with the exception of the joining sequence involving the Dδ2 and Jδ1 segments:

Vδ1 Dδ2 N TGT GCT CTT GGG GAC TTC CTA AAG GGT TCA GGT ACC ACC TAT Jδ1 CCA TGG GAA CTC ATC TTT (SEQ ID NO:7)

e) Integration into the expression vector and transfection into eukaryotic cells The digestion, with the XhoI and EcoRI restriction enzymes, of the vector pBS-SK containing the Vδ1 Cδ cDNA liberates a DNA fragment encoding the entire variable part Vδ1 Dδ2 Jδ1 and the portion of the first exon of the constant part Cδ between the joining region and the unique EcoRI site.

This DNA fragment was purified and integrated into the expression vector pKCR6 containing the soluble Vδ3 chain after it had been digested with the XhoI and EcoRI restriction enzymes. This strategy therefore made it possible to replace the variable part Vδ3 with the variable part Vδ1 and thus to construct a cDNA encoding a soluble Vδ1 chain.

The vector thus obtained was co-transfected in combination with the expression vector containing the cDNA encoding the soluble Vγ9 chain.

The procedure for transfection, screening of the producing clones and purification of the soluble TCRs produced is analogous to that described for the production of soluble TCR Vγ9 Vδ2.

2. Detection And Purification of Other Soluble Tγδ Receptors a) Detection of various soluble receptors, control of specificity In the same manner as described above, 2 IRMAs were developed with the antibody 510 as phase antibody and with the antibodies 360 and 389 as tracers. These 2 IRMAs were tested on the supernatants of CHOs transfected with the genes Vγ9/Vδ2, Vγ9/Vδ3, Vγ8/Vδ2. Only the tracers corresponding to the transfected V give a signal, thus providing a good control of specificity.

b) Development of a general method of purification

The purification described previously for isolating the Vγ9Vδ2 receptor consisted of an immunopurification with an anti-Vγ9 antibody (Y102 or 7B6). An affinity column of the same type but using the antibody 510 described above and which recognizes a determinant of the delta constant chain was used. The advantage of this new purification is the possibility of purifying any soluble receptor of the invention regardless of the γ, δ and even α, β variable chains which they contain. This method was first tested in order to purify the soluble receptor containing Vγ9/Vδ3.

5 mg of antibody 510 were covalently linked to 1 g of a matrix of cyanogen bromide-activated sepharose 4B beads (PHARMACIA, Upsalla, Sweden) according to the instructions of the supplier.

The supernatant from a culture of the transfectant γ9δ3 was applied to the affinity column thus formed at the rate of 10 ml/hour at room temperature. After washing with a phosphate buffered saline solution PBS (0.01M phosphate, 0.14M NaCl, pH 7.2, same flow rate), the bound material was eluted with a 0.05M titrate solution at pH 3.0. The eluted fractions were neutralized immediately with a 0.2M Tris buffer pH 9 (100 μl for 1 ml of eluate).

The fractions positive for the soluble TR activity as attested by the IRMA test were combined and concentrated to 1 μg/ml of proteins on a CENTRICON cell (30 KD barrier) (AMICON, Beverly, Mass., USA) according to the instructions of the manufacturer. This cell also made it possible to change the buffer for PBS.

The analysis of the eluted proteins was carried out by SDS-PAGE and by Western-blotting. The analysis gave slightly different results compared with γ9δ2. Indeed, under non-reducing conditions, three highly predominant bands of molecular weights 65, 68, 70 kD, which separated into four predominant bands 32.5, 34, 36 and 40 kD [sic]. Western-blot analysis with the anti-bodies 510 (anti-Cδ) and 360 (anti-Vγ9) showed that all the predominant bands previously observed under non-reducing conditions reacted with both antibodies. Under reducing conditions, the bands reacted either with the antibody 360 or with the antibody 510.

From this analysis, it can be concluded that the material eluted from the affinity column consisted essentially of covalently linked γδ heterodimers possibly present in the form of several glycosylation isomers.

I claim:

1. Process for producing soluble T receptors, comprising co-transfecting into a host cell DNA sequences each encoding only a single peptide consisting of one of the constituent T receptor units, from which the transmembrane portion of the T receptor has been deleted.

2. Process according to claim 1, wherein VαC/VβCβ soluble T receptors are produced by co-transfecting, into a host cell, said DNA sequences each encoding a respective one of the α and β subunits of the Tαβ receptor from which the transmembrane portion of the Tαβ receptor has been deleted.

3. Process according to claim 1, wherein VγCγ/VδCδ soluble T receptors are produced by co-transfecting, into a host cell, said DNA sequences each encoding a respective one of the γ and δ subunits of the Tγδ receptor from which the transmembrane portion of the Tγδ receptor has been deleted.

4. Process according to claim 1, wherein VαC/65 /VβCδ heterodimeric soluble T receptors are produced, in which the constituent subunits are associated via a covalent bond, by co-transfecting, into a host cell, said DNA sequences each encoding a respective one of the Cγ and Cδ domains of the γ and δ subunits of the Tγδ receptor from which their transmembrane portion has been deleted, fused respectively to the DNA sequences encoding the Vα and Vβ domains of the α and β subunits of the Tαβ receptor.

5. Process according to claim 1, wherein VαCδ/VβC/65 heterodimeric soluble T receptors are produced, in which the constituent subunits are associated via a covalent bond, by co-transfecting, into a host cell, said DNA sequences each encoding a respective one of the Cγ and Cδ domains of the γ and δ subunits of the Tγδ receptor from which their transmembrane portion has been deleted, fused respectively to the DNA sequences encoding the Vβ and Vα domains of the β and α subunits of the tαβ receptor.

6. Process according to claim 1, wherein VγCγ/VαCδ hybrid soluble T receptors are produced by co-transfecting, into a host cell, a said DNA sequence encoding the γ subunit of the Tγδ receptor from which its transmembrane portion has been deleted, and a said DNA sequence encoding the Cδ domain of the δ subunit fused to a said DNA sequence encoding the Vα domain of the α subunit of the Tαβ receptor.

7. Process according to claim 1, wherein the deletion of the transmembrane portion of the constituent T receptor subunits is carried out by introducing a translational termination codon upstream of the sequences encoding the transmembrane portion of these subunits.

8. Process according to claim 7, wherein the introduction of a translational termination codon is effected by PCR directed mutagenesis.

9. Process according to claim 1, wherein the co-transfection is carried out into eukaryotic cells.

10. Process according to claim 9, wherein said eukaryotic cells are hamster ovary cells.

* * * * *